(12) United States Patent
Beyert

(10) Patent No.: US 7,797,774 B1
(45) Date of Patent: Sep. 21, 2010

(54) DIAPER CHANGING SYSTEM FOR USE IN A VEHICLE

(76) Inventor: Rosemary D. Beyert, 500 Spring Acres Cove, Niceville, FL (US) 32578

( * ) Notice: Subject to any disclaimer, the term of this patent is extended or adjusted under 35 U.S.C. 154(b) by 85 days.

(21) Appl. No.: 12/080,432

(22) Filed: Apr. 1, 2008

(51) Int. Cl.
*A45C 9/00* (2006.01)
(52) U.S. Cl. .............................................. 5/655; 5/417
(58) Field of Classification Search ................... 5/93.1, 5/97, 99.1, 655, 417; 160/127; 108/50.11; 312/108, 201; 383/4, 38; 206/2
See application file for complete search history.

(56) References Cited

U.S. PATENT DOCUMENTS

| | | | |
|---|---|---|---|
| 1,653,246 A | 12/1927 | Zichy | |
| 2,540,165 A | 2/1951 | Fiel | |
| 2,584,435 A | 2/1952 | Doerr | |
| 3,489,194 A | 1/1970 | Hoover | |
| 3,732,955 A | 5/1973 | Carter et al. | |
| 4,068,786 A | 1/1978 | Taniguchi | |
| 4,154,323 A | 5/1979 | Sneider | |
| 4,781,277 A | 11/1988 | Lim | |
| 4,792,024 A | 12/1988 | Morton et al. | |
| 5,062,557 A | 11/1991 | Mahvi et al. | |
| 5,926,881 A | 7/1999 | Madison | |
| 5,961,216 A * | 10/1999 | Quinn et al. | 383/4 |
| 6,192,535 B1 * | 2/2001 | Warner et al. | 5/93.1 |
| 6,298,509 B1 | 10/2001 | Vickers | |
| 6,298,993 B1 | 10/2001 | Kalozdi | |
| 6,327,726 B1 | 12/2001 | Weber | |
| 6,421,856 B1 | 7/2002 | Furnback | |
| 6,539,563 B1 * | 4/2003 | Hsia | 5/93.1 |
| 6,694,552 B1 | 2/2004 | Vickers | |
| 6,742,635 B2 | 6/2004 | Hirshberg | |
| 6,745,895 B2 | 6/2004 | Silvers | |
| 6,860,550 B2 | 3/2005 | Wojcik | |
| 2006/0150324 A1 | 7/2006 | Jackson et al. | |

\* cited by examiner

*Primary Examiner*—Fredrick Conley
(74) *Attorney, Agent, or Firm*—Peter Loffler

(57) ABSTRACT

A carryall baby changing station has a body member with an open top and a series of internal cavities each designed and dimensioned to hold a needed changing product. One or more of the cavities has a plate that biases that cavity's contents either sidewardly or upwardly. Some of the cavities may have a removable cover overtop the cavity. One or more pads are attached to a side wall of the body member and capable of folding and unfolding for laying a child thereon. A receptacle is attached to an end of the body member and holds a trash liner. A cover is attached to the body member and is capable of being removably placed overtop the body member and zipped into such position.

20 Claims, 9 Drawing Sheets

DIAPER CHANGING SYSTEM FOR USE IN A VEHICLE

BACKGROUND OF THE INVENTION

1. Field of the Invention

The present invention relates to a diaper changing station and more specifically to a carrying case that holds various items of infant and toddler care wherein the case is capable of being unfolded and laid upon an appropriate surface such as the back deck of a sports utility vehicle in order for the case to act as a convenient diaper changing station.

2. Background of the Prior Art

Every parent knows that one of the guarantees of having small children is the need to change diapers with regular frequency. A diaper that needs changing at home typically presents no problem. A diaper changing station is laid out and all of the needs for changing the diaper, including wipes, fresh diapers, a disposal for the used diapers, powders, etc., are all present and handy for easy access. The diaper is quickly changed, the old one disposed of, and the child is back on his or her way.

A more challenging situation occurs when the diaper needs to be changed on the road, and in today's hectic world, such needs tend to occur often. Any parent or guardian that has attempted to change a diaper in a vehicle, appreciates the difficulty in such an undertaking. As the vehicle is not overly baby proof, the caretaker must keep a good hold of the child in order to prevent injury while at the same time actually changing the diaper. In the limited confines of a vehicle, such a task is not easy. Additionally, the caretaker must fumble around in a carrying bag to find the necessary paraphernalia in order to get the job done. As Murphy's Law may have it, the package of needed wipes is at the bottom of the carrying bag and the contents are strew over the floor of the vehicle before success is achieved in getting to the desired item. This yoga routine is played out over and over again in many people's lives.

To address this problem, baby changing stations have been proposed wherein a changing station is part of the vehicle, typically the seat. These stations provide an area that has the needed tools to get the diaper changing job done in an organized and efficient manner all within the confines of the vehicle. However, some such systems, by being built into the vehicle directly add significantly to the overall vehicle costs making such systems cost-prohibitive to many consumers. Add on systems are likewise expensive to obtain and install and many vehicle owners are reluctant to modify their vehicles to accommodate such systems. Additionally, many households have two or more vehicles for transport of their children so that the above problems are magnified.

What is needed is a portable diaper changing station that allows a vehicle-bound caretaker to be able to quickly and easily change the diaper of a child while in a vehicle. Such a station must hold the various items needed for diaper changing—fresh diapers, wipes, creams, powders, etc., —and allow quick and easy access to such items so that the caretaker has rapid access to the organized products. Such a diaper changing station must not require expensive modification of the vehicle, either at the factory or in the aftermarket so as to not discourage parents from obtaining such a device. The station should be portable so as to be easily transportable and must be relatively compact so as not to occupy an inordinate amount of the finite available real estate within a vehicle. Ideally, such a device should be of relatively simple design and construction so as to be relatively inexpensive to manufacture and use.

SUMMARY OF THE INVENTION

The diaper changing station for use in a vehicle of the present invention addresses the aforementioned needs in the art by providing a diaper changing station that allows a vehicle-bound caretaker to be able to quickly and easily change the diaper of a child during vehicle usage. The diaper changing station for use in a vehicle holds the various items needed for diaper changing in an organized manner allowing quick and easy access to such items for the caretaker. The diaper changing station for use in a vehicle does not require expensive modification of the vehicle, either at the factory or in the aftermarket, thereby not discouraging parents from obtaining and installing the present invention. The diaper changing station for use in a vehicle is relatively compact and is portable so as to be easily transportable and only occupies a relatively small amount of the finite real estate that is available within a vehicle. The diaper changing station for use in a vehicle is of relatively simple design and construction making the device relatively inexpensive to manufacture and use.

The diaper changing station for use in a vehicle of the present invention is comprised of a body member that has a base, a first side, an opposing second side, a first end wall, an opposing second end wall, an internal space, and an open top. An internal wall is disposed within the body member in order to segregate the internal space of the body member into at least two separate cavities. The internal wall may be monolithic with the rest of the body member or may be a separate insert. A first changing pad is attached to the first side wall proximate the base such that first changing pad is capable of being folded against the first side wall and held thereat by a first set of cooperating hook and loop fastener portions attached to the first changing pad and to the first side wall. A cover is attached to the body member and is positionable into a closed position overtop the open top of the body member such that a zipper system that attaches the cover to remainder main body member maintains the cover in the closed position. A notch is disposed within the first end wall and extends downwardly from the open top while a carrying handle is attached to the first end wall below the notch. A plate is disposed within a respective one of the cavities while a spring has a first end that abuts the base of the body member and a second end that abuts an underside of the plate so as to bias the plate toward the open top of the body member. A cover is removably positionable over this respective one of the cavities. The cover has a slot. Additional covers with slots may be provided to cover other cavities. Another plate disposed within another respective one of the cavities such that another spring has a first end that abuts the internal wall (or side or end wall of the body member) and a second end that abuts an underside of this second plate so as to bias this second plate away from the internal wall whereat the first end of this second spring is attached. A receptacle is removably attached to the second end wall of the body member, the receptacle being collapsible. A liner is removably insertable into the receptacle. A netting member is attached to the first side wall so as to define a pocket between the netting member and the first side wall. An opening is disposed within the first end wall leading to a respective one of the cavities. A second changing pad may be provided and is attached to the second side wall proximate the base such that the second changing pad is capable of being folded against the second side wall and held thereat by a second set of cooperating hook and loop fastener portions.

BRIEF DESCRIPTION OF THE DRAWINGS

Similar reference numerals refer to similar parts throughout the several views of the drawings.

DESCRIPTION OF THE PREFERRED EMBODIMENT

Figure 1:
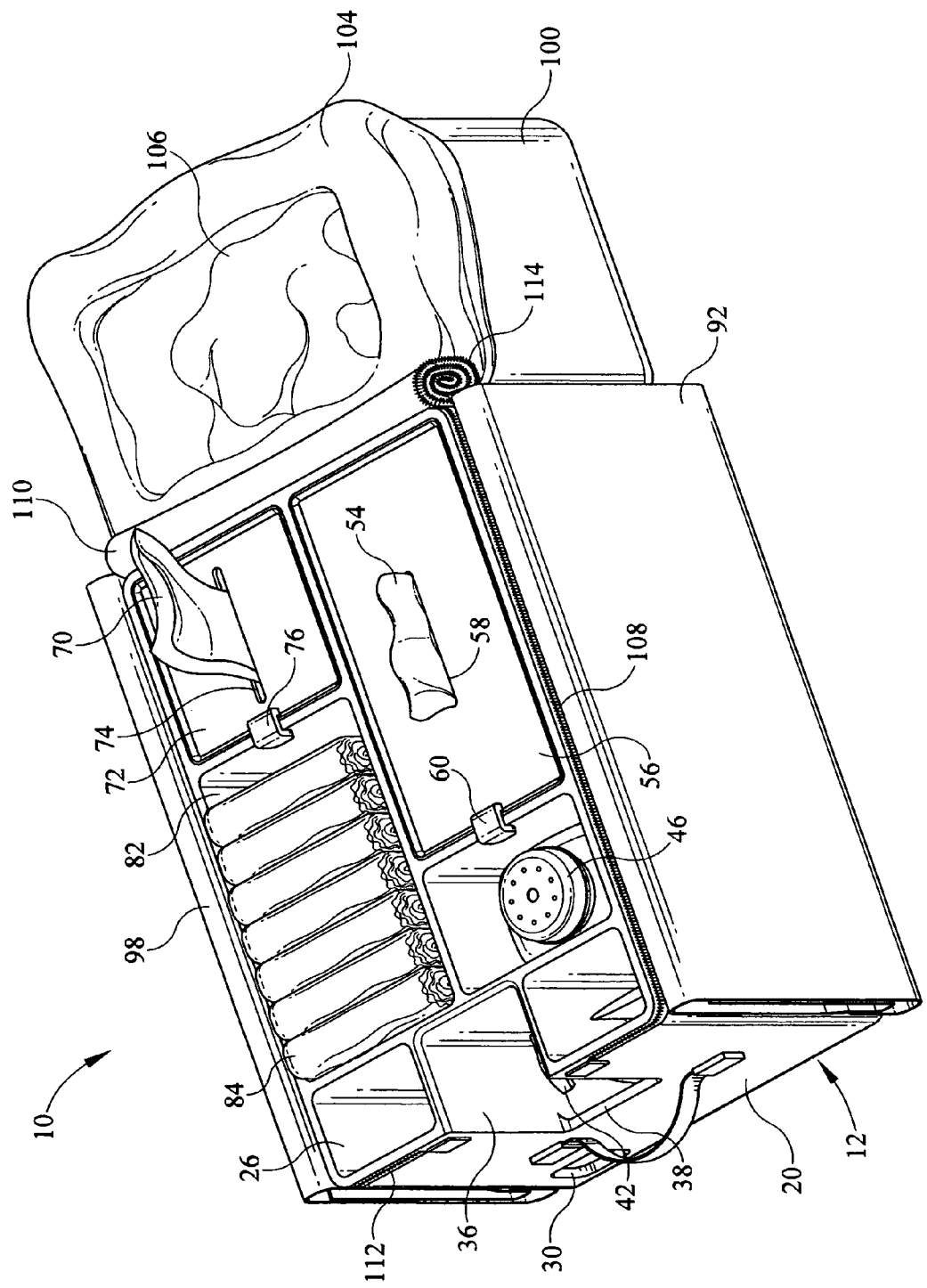
FIG. 1 is a perspective view of the diaper changing station for use in a vehicle of the present invention.
Figure 2:
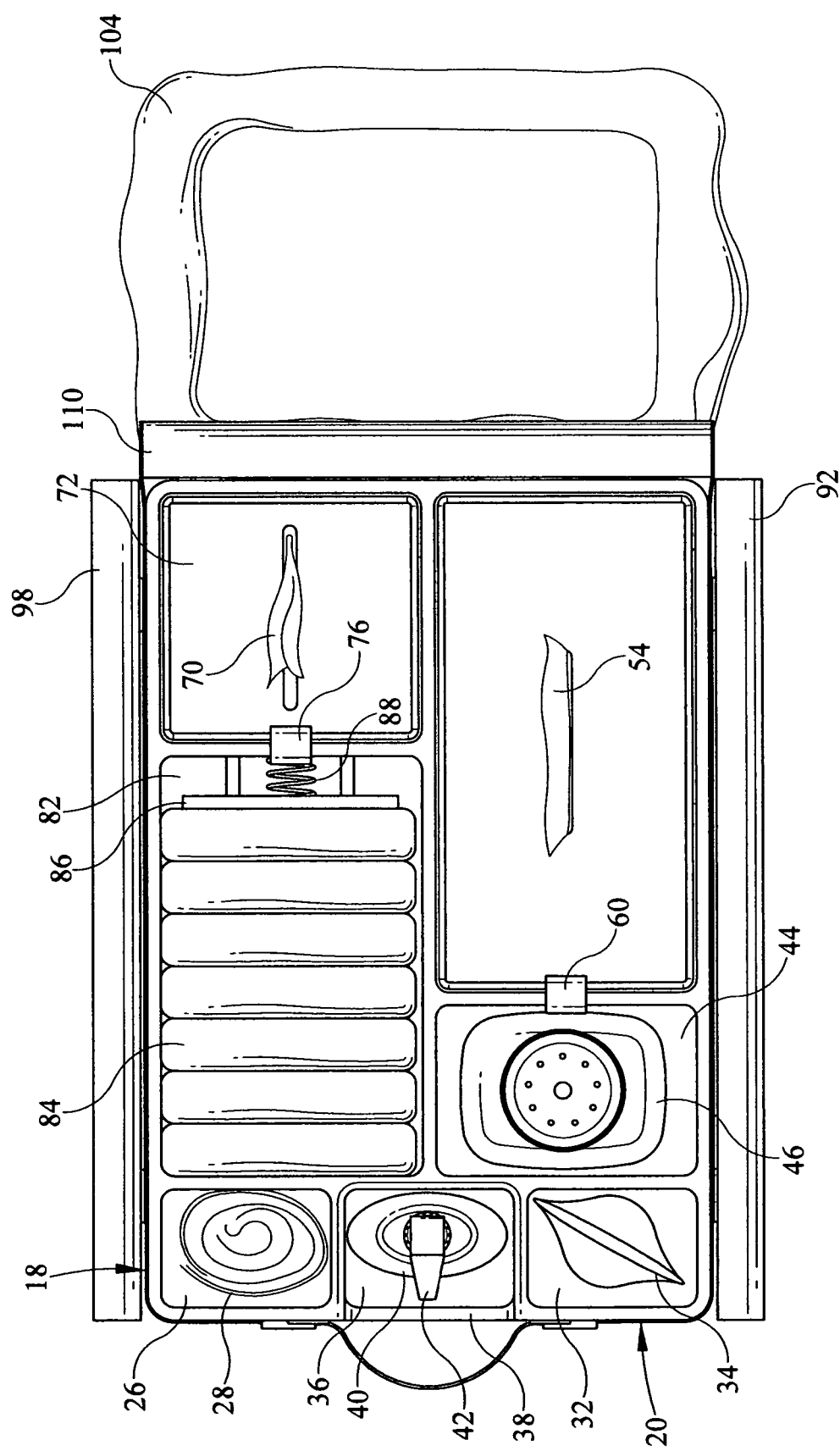
FIG. 2 is a top plan view of the diaper changing station for use in a vehicle.
Figure 3:
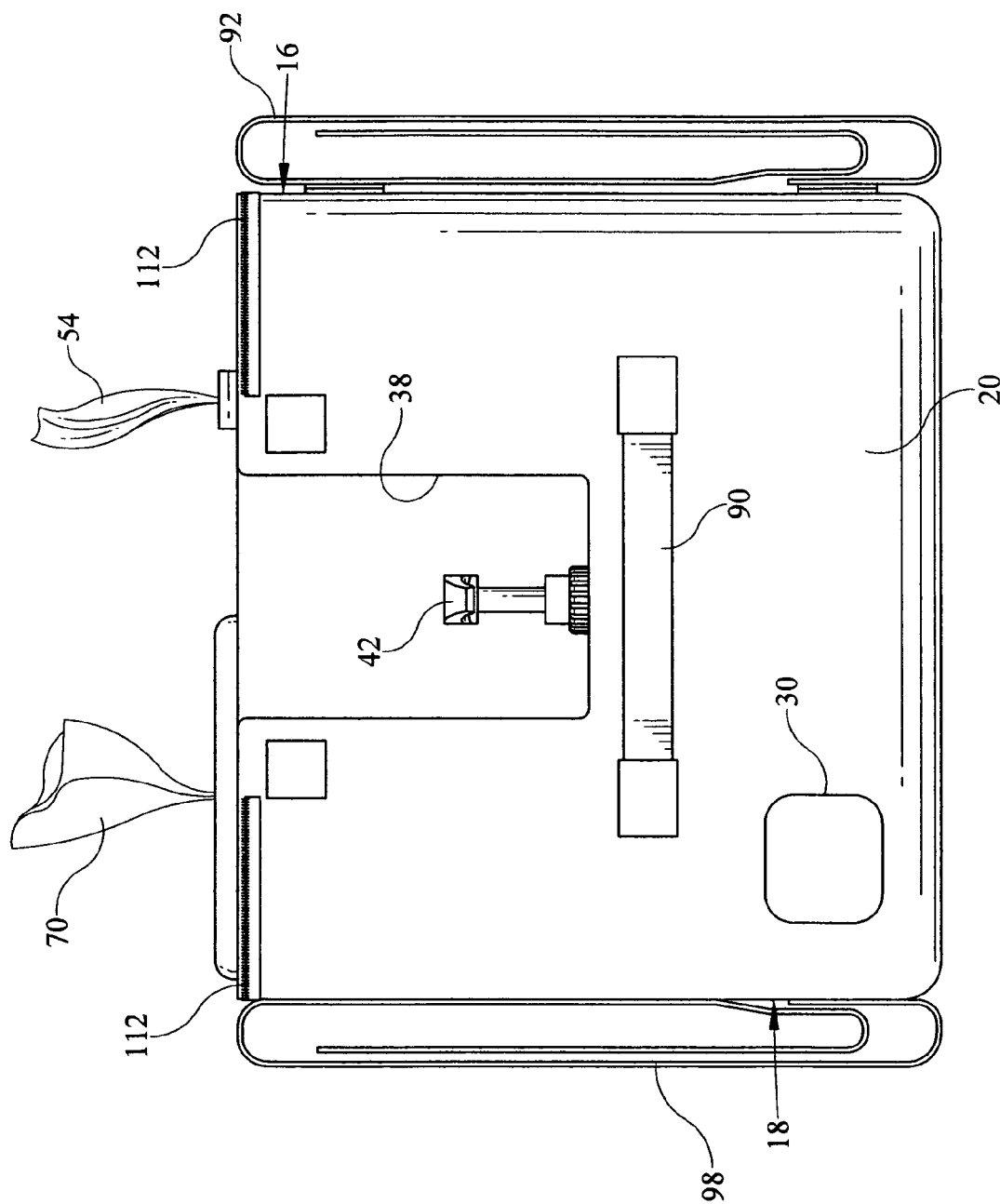
FIG. 3 is a side elevation view of the diaper changing station for use in a vehicle.
Figure 4:
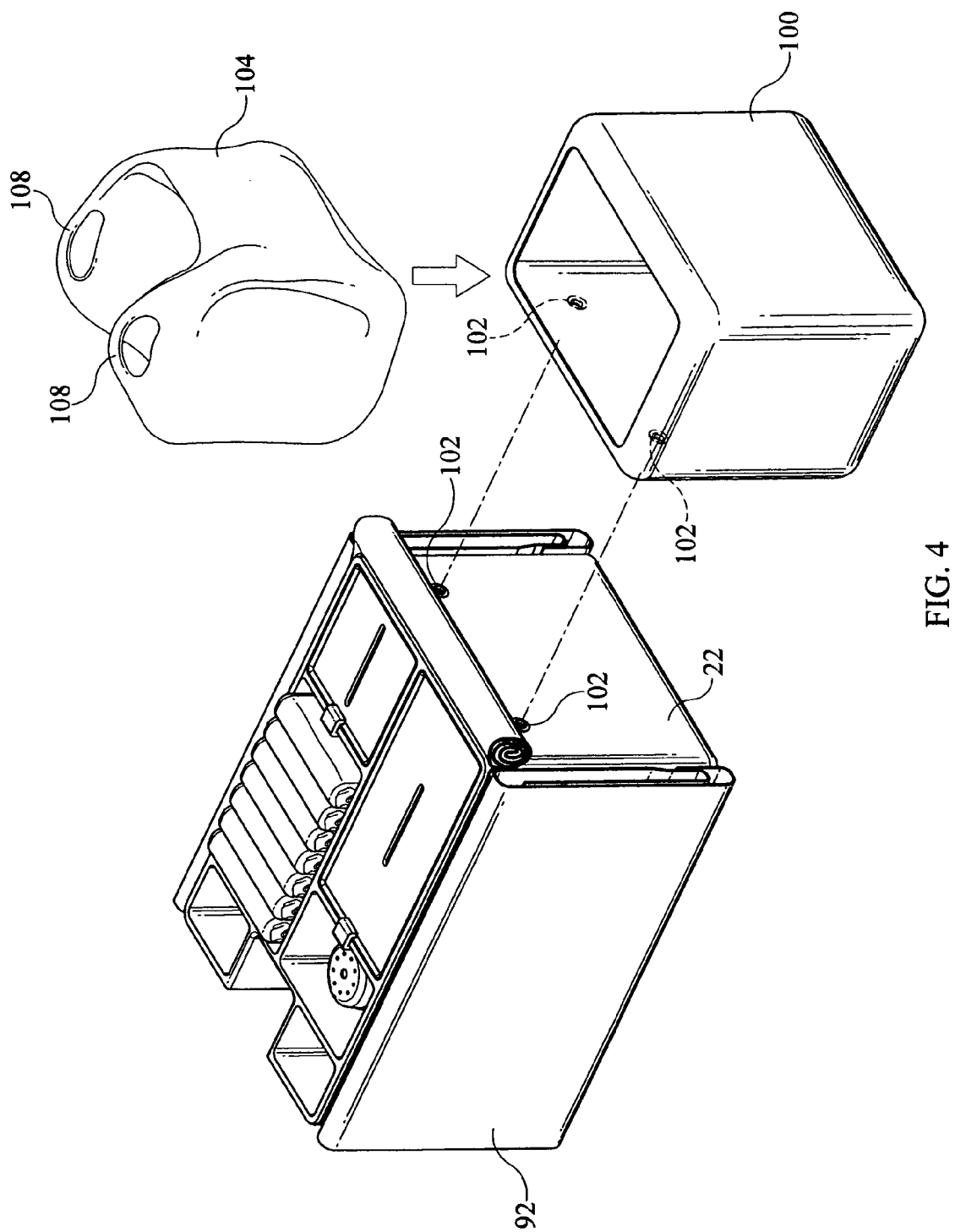
FIG. 4 is a perspective view of the diaper changing station for use in a vehicle illustrating the detachment of the disposal system.
Figure 5:
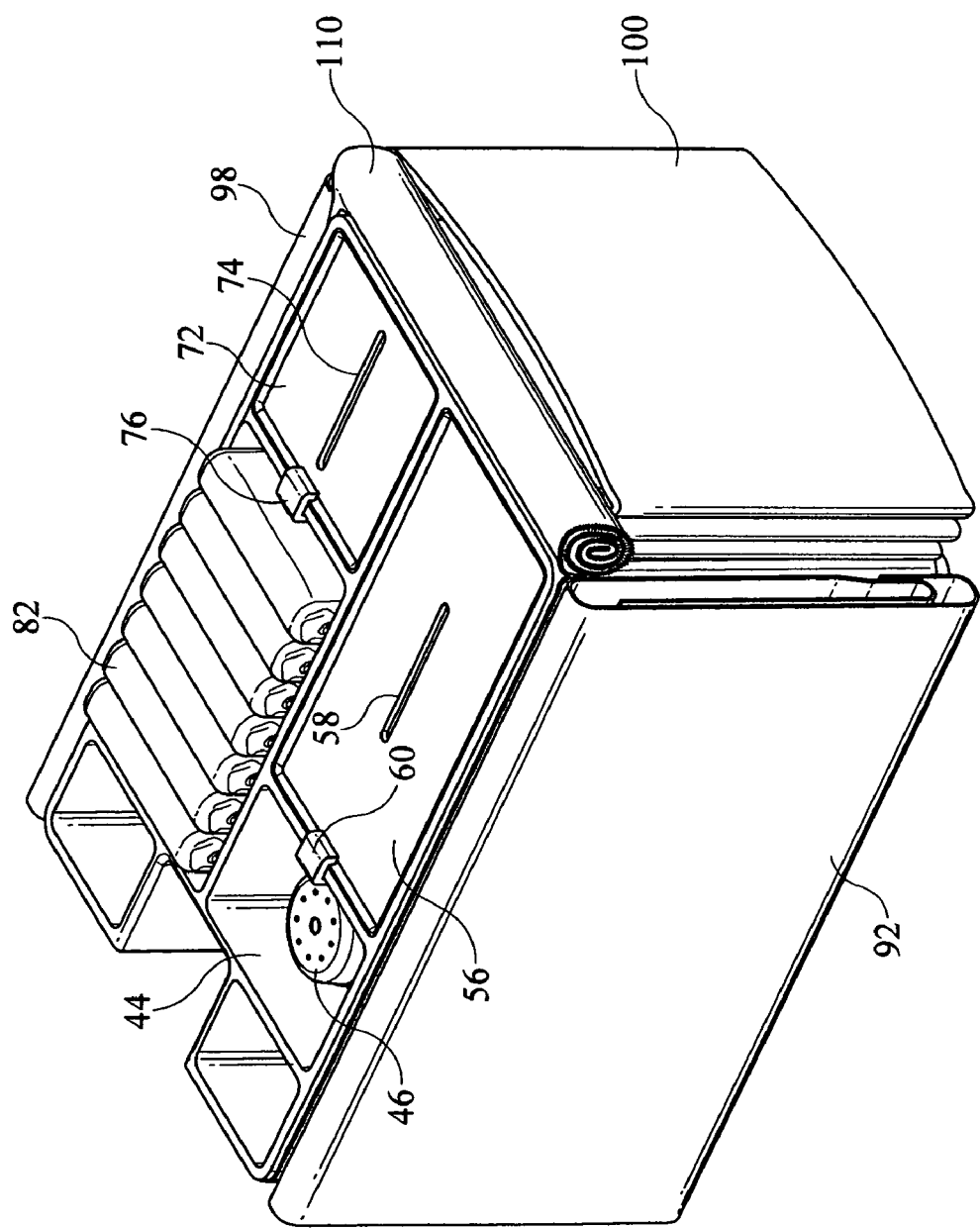
FIG. 5 is a perspective view of the diaper changing station for use in a vehicle illustrating the waste receptacle of the disposal system in a collapsed position.
Figure 6:
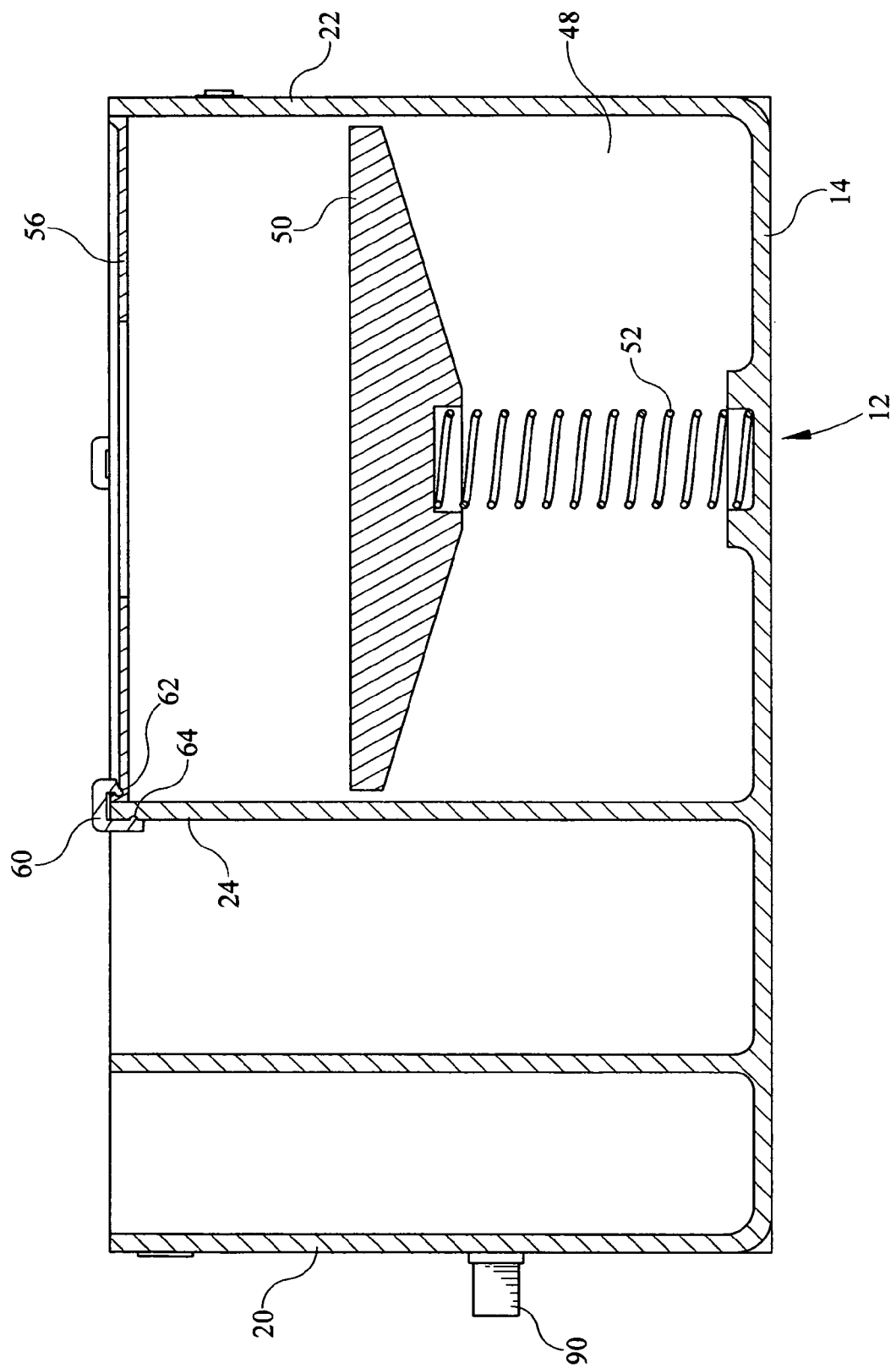
FIG. 6 is a sectional view of the diaper changing station for use in a vehicle taken along line 6-6 in FIG. 8.
Figure 7:
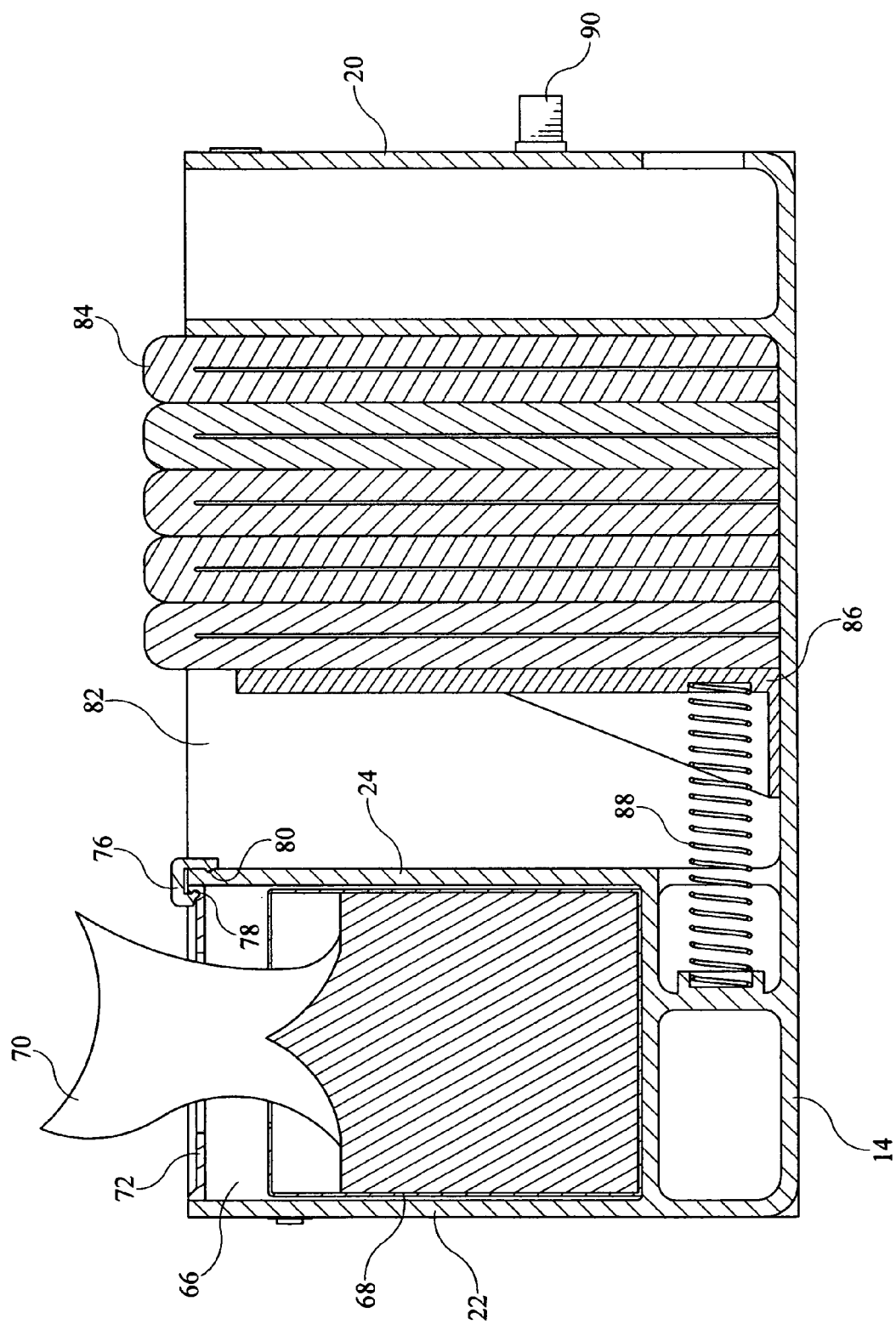
FIG. 7 is a sectional view of the diaper changing station for use in a vehicle taken along line 7-7 in FIG. 8.
Figure 8:
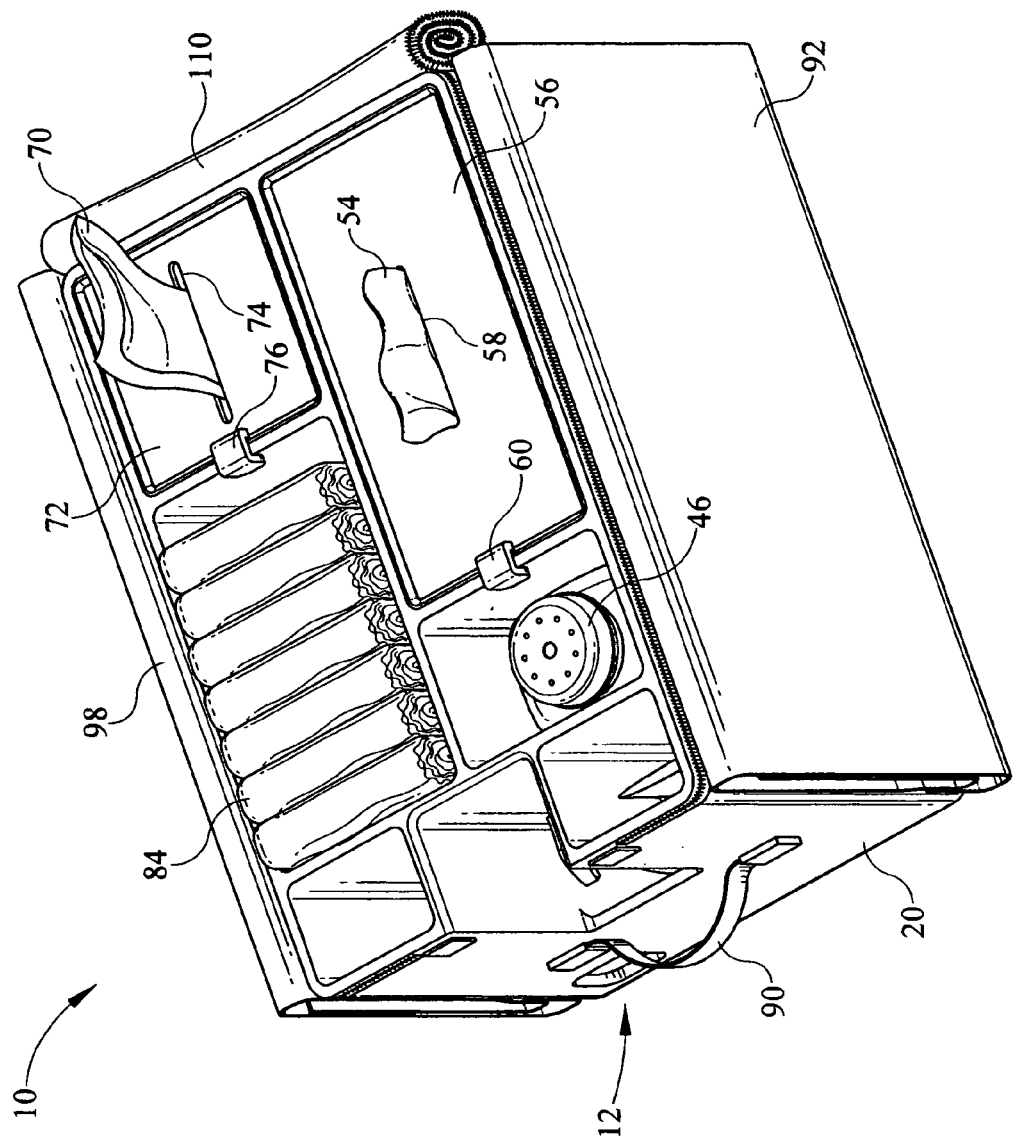
FIG. 8 is a perspective view of the diaper changing station for use in a vehicle illustrated with the disposal system detached.

Referring now to the drawings, it is seen that the diaper changing station for use in a vehicle of the present invention, generally denoted by reference numeral 10, is comprised of a main body member 12 having a base 14, a first side wall 16, a second side wall 18, a first end wall 20, and a second end wall 22 and an open top, the main body member 12 being made from an appropriate sturdy material such as plastic. As seen, a series of internal walls 24 are disposed within the main body member 12 in order to form a series of cavities therein, each cavity being used to hold an appropriate changing item.

As seen a first cavity 26 may hold plastic disposal bags 28 therein, such that a lower opening 30 may be located on the first end wall 20 in order to provide easy access for bag 28 retrieval.

A second cavity 32 is provided and may hold an appropriate container 34 of cream or ointment or similar material, while a third cavity 36 is disposed between the first cavity 30 and the second cavity 32 with a notch 38 located on the first end wall 20 so that an appropriate pump dispenser 40 may be held in this third cavity 36 so that the dispensing nozzle 42 of the pump dispenser 40 can be easily accessed through the notch 38.

A fourth cavity 44 is provided such that this fourth cavity 44 may hold a container 46 of baby powder or similar article.

A fifth cavity 48 is provided such that a plate 50 is disposed within the fifth cavity 48. A spring 52 is disposed between the base 14 of the main body member 12 and the underside of the first plate 50 in order to bias the first plate 50 toward the open top of the main body member 12. As seen, a series of moist towelettes 54 are disposed on the top side of the plate 50 so that the plate 50 biases the towelettes 54 toward the open top of the main body member 12. A first cover 56 is positioned overtop this fifth cavity 48 such that the cover 56 has a first slot 58 therein that allows a towelette 54 to protrude through the first slot 58 so as to allow a user to retrieve towelettes 54 one at a time. The first cover 56 is secured to the top of the fifth cavity 48 by the use of the illustrated first clip 60 that clips to a notch 62 in the first cover 56 and to another notch 64 on the internal wall 24 within the fourth cavity 44, so that when loading of the fifth cavity 48 is required, the first clip 60 is removed allowing the first cover 56 to be removed. Towelettes 54 are placed onto the first plate 50 which is pushed downwardly as needed. Once the fifth cavity 48 is filled as needed, the first cover 56 is replaced overtop the fifth cavity 48, the first clip 60 is clipped into place in order to hold the first cover 56 onto the main body member 12, and the uppermost towelette 54 is fed through the first slot 58 of the first cover 56 is order to allow the orderly dispensing of towelettes 54. As towelettes 54 are dispensed, the first plate 50 biases the remaining towelettes 54 toward the first slot 58 or the first cover 56.

A sixth cavity 66 is used to hold a stack or box 68 of napkins 70 or similar items such that a second cover 72 having a second slot 74 is positioned overtop this sixth cavity 66. Similarly to the first cover 56, the second cover 72 is maintained in covering relationship with the sixth cavity 66 by providing a second clip 76 that clips into a notch 78 located on the second cover 72 and to another notch 80 located on the internal wall 24 within a seventh cavity 82 discussed infra. In order to fill the sixth cavity 66, the second clip 76 is unclipped, and the second cover 70 is removed. A box 68 or just a stack of napkins 70 is placed into the sixth cavity 66 and the second cover 72 is replaced overtop the sixth cavity 66, the second clip 76 is clipped into place in order to hold the second cover 72 onto the main body member 12, and the uppermost napkin 70 is fed through the second slot 74 of the second cover 72 is order to allow the orderly dispensing of napkins 70.

The seventh cavity 82 is designed to hold diapers 84 such that a second plate 86 is disposed within the seventh cavity 82 and has a spring 88 that abuts a first side of the second plate 86 and a wall underneath the sixth cavity 66 within the main body member 12. The other side of second plate 86 presses against the endmost diaper 84 such that the spring 88 biases the second plate 86 toward the diapers 84 and thus biases the diapers 84 into the illustrated upright position.

Although the invention is disclosed with respect to the seven illustrated cavities, it is expressly noted that more or less cavities may be used and in differing configurations depending on the amount and style of the items that are to be stored, in keeping with the scope and spirit of the present invention.

A carrying handle 90 is attached to the first end wall 20 just below the notch 38 of the third cavity 36.

Figure 9:
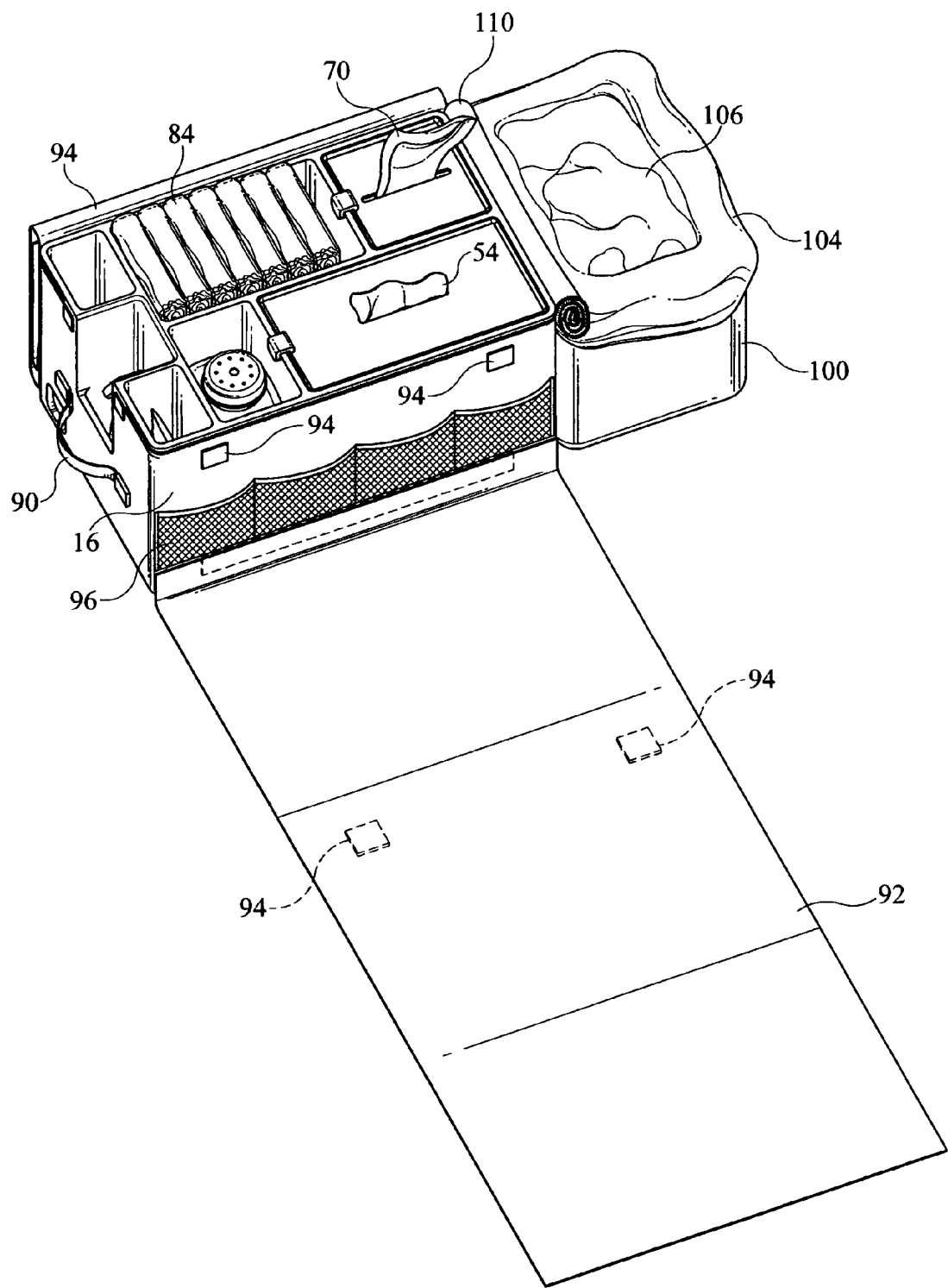
FIG. 9 is a perspective view of the diaper changing station for use in a vehicle with one of the changing pads deployed.

A first changing pad 92 is attached to the first sidewall 16 proximate the base 14 such that the first changing pad 92 may be folded into a stowed position with appropriate cooperating hook and loop fasteners 94 (including the newer hook and dart) attached to the first side wall 16 of the body member 12 proximate the open top thereof, and to an underside of the first changing pad 92. In the stowed position, the first changing pad 92 is folded into place against the first side wall 16 such that the hook and loop fasteners 94 hold the first changing pad 92 in this stowed position. When the first changing pad 92 is needed, the hook and loop fasteners 94 are detached from one another and the first changing pad 92 is unfolded and used as desired, as best illustrated in FIG. 9. Once the first changing pad 92 is no longer needed, it is folded back into the stowed position and the hook and loop fasteners 94 are appropriately rejoined. As seen in FIG. 9, a netting holder 96 is attached to the first sidewall 16 such that the netting holder 94 creates one or more holding pockets.

A second changing pad 98 may be attached to the second side wall 18 in similar fashion to the attachment of the first changing pad 92 to the first side wall 16.

A collapsible waste receptacle 100 is removably attached to the second end wall 22 by the illustrated snaps 102 or similar attachment mechanism. A trash liner 104 is removably insertable into the waste receptacle 100 and is designed to hold used diapers 106 and other debris so that when the trash liner 104 is full, it is removed, with the assistance of the illustrated handles 108, and disposed of as appropriate, with a new trash liner 104 inserted into the waste receptacle 100. By being collapsible, the waste receptacle 100 can be collapsed as needed in order to compact the size of the device 10.

A roll top cover 110 is provided in order to cover the open top of the main body member 12 such that first zipper legs 112 are provided on the first side wall 16, the second side wall 18 and the first end wall 20, and second zipper legs 114 are corresponding provided on the outer periphery of the roll top cover 110 in order to allow the roll top cover 110 to be placed overtop the open top of the main body member 12 and zipped into a closed position and such that when access to the main body member 12 is desired, the roll top cover 110 is unzipped and rolled away from the open top of the main body member 12. Appropriate fasteners (hook and loop or otherwise—none illustrated) are used to hold the roll top cover 110 in its furled open position.

In order to use the diaper changing station for use in a vehicle 10 of the present invention, the various cavities are loaded with the desired supplies and a trash liner 104 is placed into the waste receptacle 100. The roll top cover 110 is placed into the closed position and the first changing pad 92 and the second changing pad 98 are each placed into their stowed position. The main body member 12 is carried by the handle 90. If access to supplies is needed, the roll top cover 110 is unzipped and unfurled and the supplies are retrieved (if only the contents of the pump dispenser 40 are needed, there is no need to unfurl the roll top cover 110, as the dispensing nozzle 42 can be depressed through the notch 38 on the first end wall 20). If the baby needed to be changed, then one of the changing pads 92 or 98 is unfolded and the baby placed thereonto. The diaper is changed with a fresh diaper 84 retrieved from the seventh cavity 82 and the used diaper 106 deposited into the trash liner 104 of the waste receptacle 100. Once the baby is appropriately changed, the changing pad used 92 or 98 is placed back into its stowed position. If desired the entire waste disposal system can be detached from the device 10 by detaching the waste receptacle 100 from the main body member 12.

While the invention has been particularly shown and described with reference to an embodiment thereof, it will be appreciated by those skilled in the art that various changes in form and detail may be made without departing from the spirit and scope of the invention.

I claim:

1. A changing station comprising:
a body member having a base, a first side, and opposing second side, a first end wall, an opposing second end wall, an internal space, and an open top;
an internal wall disposed within the body member in order to segregate the internal space of the body member into at least two separate cavities;
a first plate disposed within a respective one of the cavities;
a first spring having a first end that abuts the base of the body member and a second end that abuts an underside of the first plate so as to bias the first plate toward the open top of the body member; and
a first changing pad attached to the first side wall proximate the base.

2. The changing station as in claim 1 wherein the first changing pad is capable of being folded against the first side wall and held thereat by a first set of cooperating hook and loop fastener portions.

3. The changing station as in claim 1 further comprising a cover that is attached to the body member and is removably positionable into a closed position overtop the open top of the body member.

4. The changing station as in claim 3 wherein the cover is maintained in the closed position by providing a zipper system that attaches the cover to the remainder of the main body member.

5. The changing station as in claim 1 further comprising a notch disposed within the first end wall and extending downwardly from the open top.

6. The changing station as in claim 5 further comprising a carrying handle attached to the first end wall below the notch.

7. The changing station as in claim 1 further comprising an opening disposed within the first end wall leading to a respective one of the cavities.

8. The changing station as in claim 1 further comprising a cover removably positionable over the respective one of the cavities.

9. The changing station as in claim 8 wherein the cover has a slot.

10. The changing station as in claim 1 further comprising:
a second plate disposed within a respective another one of the cavities;
a second spring having a third end that abuts the internal wall and a fourth end that abuts an underside of the second plate so as to bias the second plate away from the internal wall whereat the third end of the second spring is attached.

11. The changing station as in claim 1 further comprising a receptacle removably attached to the second end wall of the body member.

12. The changing station as in claim 11 wherein the receptacle is collapsible.

13. The changing station as in claim 11 further comprising a liner removably insertable into the receptacle.

14. The changing station as in claim 1 further comprising a netting member attached to the first side wall so as to create a pocket between the netting member and the first side wall.

15. The changing station as in claim 1 further comprising a second changing pad attached to the second side wall proximate the base.

16. The changing station as in claim 15 wherein the second changing pad is capable of being folded against the second side wall and held thereat by a second set of cooperating hook and loop fastener portions.

17. A changing station comprising:
a body member having a base, a first side, and opposing second side, a first end wall, an opposing second end wall, an internal space, and an open top;
an internal wall disposed within the body member in order to segregate the internal space of the body member into at least two separate cavities;
a plate disposed within a respective one of the cavities;
a spring having a first end that abuts the internal wall and a second end that abuts an underside of the plate so as to bias the plate away from the internal wall whereat the first end of the spring is attached; and
a first changing pad attached to the first side wall proximate the base.

18. The changing station as in claim 17 further comprising an opening disposed within the first end wall leading to a respective one of the cavities.

19. A changing station comprising:
- a body member having a base, a first side, and opposing second side, a first end wall, an opposing second end wall, an internal space, and an open top;
- an internal wall disposed within the body member in order to segregate the internal space of the body member into at least two separate cavities;
- an opening disposed within the first end wall leading to a respective one of the cavities; and
- a first changing pad attached to the first side wall proximate the base.

20. The changing station as in claim 19 further comprising a receptacle removably attached to the second end wall of the body member.

* * * * *